(12) United States Patent
Rosinko

(10) Patent No.: US 10,213,547 B2
(45) Date of Patent: Feb. 26, 2019

(54) SAFETY PROCESSOR FOR A DRUG DELIVERY DEVICE

(71) Applicant: Tandem Diabetes Care, Inc., San Diego, CA (US)

(72) Inventor: Michael Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 292 days.

(21) Appl. No.: 15/336,930

(22) Filed: Oct. 28, 2016

(65) Prior Publication Data

US 2017/0043085 A1 Feb. 16, 2017

Related U.S. Application Data

(63) Continuation of application No. 14/581,461, filed on Dec. 23, 2014, now Pat. No. 9,486,571.

(60) Provisional application No. 61/920,940, filed on Dec. 26, 2013.

(51) Int. Cl.
| | |
|---|---|
| *A61M 5/142* | (2006.01) |
| *G16H 40/40* | (2018.01) |
| *G06F 19/00* | (2018.01) |
| *G08C 17/02* | (2006.01) |

(52) U.S. Cl.
CPC ..... *A61M 5/14244* (2013.01); *G06F 19/3418* (2013.01); *G06F 19/3468* (2013.01); *G08C 17/02* (2013.01); *G16H 40/40* (2018.01); *A61M 2205/12* (2013.01); *A61M 2205/3576* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2230/201* (2013.01); *G08C 2201/93* (2013.01)

(58) Field of Classification Search
None
See application file for complete search history.

(56) References Cited

U.S. PATENT DOCUMENTS

| | | | |
|---|---|---|---|
| 5,078,683 | A | 1/1992 | Sancoff et al. |
| 5,429,602 | A | 7/1995 | Hauser |
| 5,497,772 | A | 3/1996 | Schulman et al. |
| 5,582,593 | A | 12/1996 | Hultman |
| 5,660,163 | A | 8/1997 | Schulman et al. |
| 5,719,761 | A | 2/1998 | Gatti et al. |
| 5,759,199 | A | 6/1998 | Snell et al. |
| 5,885,211 | A | 3/1999 | Eppstein et al. |
| 5,935,099 | A | 8/1999 | Peterson et al. |
| 6,070,761 | A | 6/2000 | Bloom et al. |

(Continued)

FOREIGN PATENT DOCUMENTS

| | | |
|---|---|---|
| KR | 20090085114 A | 8/2009 |
| WO | WO 2008127694 A1 | 10/2008 |
| WO | WO 2013184896 A1 | 12/2013 |

OTHER PUBLICATIONS

Search Report dated Aug. 10, 2017 for EP Application No. 14873200.1, 8 pages.

(Continued)

*Primary Examiner* — Daniell L Negron
(74) *Attorney, Agent, or Firm* — Patterson Thuente Pedersen, P.A.

(57) ABSTRACT

A system and method provide for enhanced reliability and safety of programming and/or operating a medical device, such as an infusion pump. A safety processor can check whether an operating command is within acceptable parameters.

20 Claims, 7 Drawing Sheets

(56) References Cited

U.S. PATENT DOCUMENTS

| | | |
|---|---|---|
| 6,142,939 A | 11/2000 | Eppstein et al. |
| 6,241,704 B1 | 6/2001 | Peterson et al. |
| 6,427,088 B1 | 7/2002 | Bowman, IV et al. |
| 6,442,433 B1 | 8/2002 | Linberg |
| 6,468,242 B1 | 10/2002 | Wilson et al. |
| 6,471,689 B1 | 10/2002 | Joseph et al. |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,577,899 B2 | 6/2003 | Lebel et al. |
| 6,585,644 B2 | 7/2003 | Lebel et al. |
| 6,585,707 B2 | 7/2003 | Cabiri et al. |
| 6,589,229 B1 | 7/2003 | Connelly et al. |
| 6,599,281 B1 | 7/2003 | Struys et al. |
| 6,605,072 B2 | 8/2003 | Struys et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,659,948 B2 | 12/2003 | Lebel et al. |
| 6,666,821 B2 | 12/2003 | Keimel |
| 6,668,196 B1 | 12/2003 | Villegas et al. |
| 6,687,546 B2 | 2/2004 | Lebel et al. |
| 6,694,191 B2 | 2/2004 | Starkweather et al. |
| 6,733,446 B2 | 5/2004 | Lebel et al. |
| 6,740,072 B2 | 5/2004 | Starkweather et al. |
| 6,740,075 B2 | 5/2004 | Lebel et al. |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,772,331 B1 | 8/2004 | Hind et al. |
| 6,780,156 B2 | 8/2004 | Haueter et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,821,484 B1 | 11/2004 | Gregersen |
| 6,872,200 B2 | 3/2005 | Mann et al. |
| 6,873,268 B2 | 3/2005 | Lebel et al. |
| 6,936,029 B2 | 8/2005 | Mann et al. |
| 6,950,708 B2 | 9/2005 | Bowman, IV et al. |
| 6,958,691 B1 | 10/2005 | Anderson et al. |
| 6,958,705 B2 | 10/2005 | Lebel et al. |
| 6,970,741 B1 | 11/2005 | Whitehurst et al. |
| 6,970,742 B2 | 11/2005 | Mann et al. |
| 6,974,437 B2 | 12/2005 | Lebel et al. |
| 6,979,326 B2 | 12/2005 | Mann et al. |
| 6,997,920 B2 | 2/2006 | Mann et al. |
| 7,024,245 B2 | 4/2006 | Lebel et al. |
| 7,025,743 B2 | 4/2006 | Mann et al. |
| 7,092,796 B2 | 8/2006 | Vanderveen |
| 7,109,878 B2 | 9/2006 | Mann et al. |
| 7,156,808 B2 | 1/2007 | Quy |
| 7,171,274 B2 | 1/2007 | Starkweather et al. |
| 7,181,505 B2 | 2/2007 | Haller et al. |
| 7,198,603 B2 | 4/2007 | Penner et al. |
| 7,256,888 B2 | 8/2007 | Staehr et al. |
| 7,278,983 B2 | 10/2007 | Ireland et al. |
| 7,344,507 B2 | 3/2008 | Briggs et al. |
| 7,347,819 B2 | 3/2008 | Lebel et al. |
| 7,347,836 B2 | 3/2008 | Peterson et al. |
| 7,356,382 B2 | 4/2008 | Vanderveen |
| 7,369,635 B2 | 5/2008 | Spital et al. |
| 7,399,277 B2 | 7/2008 | Saidara et al. |
| 7,440,806 B1 | 10/2008 | Whitehurst et al. |
| 7,471,994 B2 | 12/2008 | Ford et al. |
| 7,481,759 B2 | 1/2009 | Whitehurst et al. |
| 7,483,743 B2 | 1/2009 | Mann et al. |
| 7,491,187 B2 | 2/2009 | Van Den Berghe et al. |
| 7,493,171 B1 | 2/2009 | Whitehurst et al. |
| 7,497,827 B2 | 3/2009 | Brister et al. |
| 7,558,629 B2 | 7/2009 | Keimel et al. |
| 7,591,801 B2 | 9/2009 | Brauker et al. |
| 7,654,127 B2 | 2/2010 | Krulevitch et al. |
| 7,654,976 B2 | 2/2010 | Peterson et al. |
| 7,668,731 B2 | 2/2010 | Martucci et al. |
| 7,678,071 B2 | 3/2010 | Lebel et al. |
| 7,711,402 B2 | 5/2010 | Shults et al. |
| 7,713,240 B2 | 5/2010 | Istoc et al. |
| 7,717,903 B2 | 5/2010 | Estes et al. |
| 7,737,581 B2 | 6/2010 | Spurlin et al. |
| 7,766,829 B2 | 8/2010 | Sloan et al. |
| 7,782,192 B2 | 8/2010 | Jeckelmann et al. |
| 7,785,313 B2 | 8/2010 | Mastrototaro |
| 7,801,596 B2 | 9/2010 | Fischell et al. |
| 7,811,279 B2 | 10/2010 | John |
| 7,815,602 B2 | 10/2010 | Mann et al. |
| 7,815,622 B2 | 10/2010 | Istoc et al. |
| 7,819,843 B2 | 10/2010 | Mann et al. |
| 7,831,310 B2 | 11/2010 | Lebel et al. |
| 7,835,927 B2 | 11/2010 | Schlotterbeck et al. |
| 7,875,022 B2 | 1/2011 | Wenger et al. |
| 7,901,394 B2 | 3/2011 | Ireland et al. |
| 7,931,613 B2 | 4/2011 | Haueter et al. |
| 7,942,844 B2 | 5/2011 | Moberg et al. |
| 7,944,366 B2 | 5/2011 | Krulevitch et al. |
| 7,979,136 B2 | 7/2011 | Young et al. |
| 7,983,745 B2 | 7/2011 | Hatlestad et al. |
| 7,985,330 B2 | 7/2011 | Wang et al. |
| 7,999,674 B2 | 8/2011 | Kamen |
| 8,002,700 B2 | 8/2011 | Ferek-Petric et al. |
| 8,005,688 B2 | 8/2011 | Coffman et al. |
| 8,020,564 B2 | 9/2011 | Batch |
| 8,021,299 B2 | 9/2011 | Miesel et al. |
| 8,062,249 B2 | 11/2011 | Wilinska et al. |
| 8,065,161 B2 | 11/2011 | Howard et al. |
| 8,095,123 B2 | 1/2012 | Gray |
| 8,099,074 B2 | 1/2012 | Ebner et al. |
| 8,106,534 B2 | 1/2012 | Spurlin et al. |
| 8,109,921 B2 | 2/2012 | Estes et al. |
| 8,117,481 B2 | 2/2012 | Anselmi et al. |
| 8,118,770 B2 | 2/2012 | Galley et al. |
| 8,121,689 B2 | 2/2012 | Kalgren et al. |
| 8,123,717 B2 | 2/2012 | Weinert et al. |
| 8,133,197 B2 | 3/2012 | Blomquist et al. |
| 8,140,312 B2 | 3/2012 | Hayter et al. |
| 8,152,764 B2 | 4/2012 | Istoc et al. |
| 8,152,789 B2 | 4/2012 | Starkweather et al. |
| 8,182,462 B2 | 5/2012 | Istoc et al. |
| 8,202,267 B2 | 6/2012 | Field et al. |
| 8,206,350 B2 | 6/2012 | Mann et al. |
| 8,206,378 B1 | 6/2012 | Kalpin et al. |
| 8,234,128 B2 | 7/2012 | Martucci et al. |
| 8,250,483 B2 | 8/2012 | Blomquist |
| 8,257,300 B2 | 9/2012 | Budiman et al. |
| 8,269,634 B2 | 9/2012 | Fischell et al. |
| 8,285,328 B2 | 10/2012 | Caffey et al. |
| 8,287,487 B2 | 10/2012 | Estes |
| 8,287,495 B2 | 10/2012 | Michaud et al. |
| 8,294,581 B2 | 10/2012 | Kamen |
| 8,298,184 B2 | 10/2012 | DiPerna et al. |
| 8,308,680 B1 | 11/2012 | Chawla |
| 8,311,749 B2 | 11/2012 | Brauker et al. |
| 8,323,188 B2 | 12/2012 | Tran |
| 8,344,847 B2 | 1/2013 | Moberg et al. |
| 8,348,885 B2 | 1/2013 | Moberg et al. |
| 8,376,943 B2 | 2/2013 | Kovach et al. |
| 8,377,031 B2 | 2/2013 | Hayter et al. |
| 8,380,536 B2 | 2/2013 | Howard et al. |
| 8,382,703 B1 | 2/2013 | Abdelaal |
| 8,395,581 B2 | 3/2013 | Gråskov et al. |
| 8,414,523 B2 | 4/2013 | Blomquist et al. |
| 8,414,557 B2 | 4/2013 | Istoc et al. |
| 8,444,595 B2 | 5/2013 | Brukalo et al. |
| 8,449,523 B2 | 5/2013 | Brukalo et al. |
| 8,451,230 B2 | 5/2013 | Celentano et al. |
| 8,452,413 B2 | 5/2013 | Young et al. |
| 8,454,510 B2 | 6/2013 | Yodfat et al. |
| 8,454,554 B2 | 6/2013 | Reinke et al. |

(56) References Cited

U.S. PATENT DOCUMENTS

| | | |
|---|---|---|
| 8,454,576 B2 | 6/2013 | Mastrototaro et al. |
| 8,456,301 B2 | 6/2013 | Fennell et al. |
| 8,469,920 B2 | 6/2013 | Mernoe et al. |
| 8,472,913 B2 | 6/2013 | Ebner et al. |
| 8,491,566 B2 | 7/2013 | Ramey et al. |
| 8,502,662 B2 | 8/2013 | Pohlman et al. |
| 8,517,987 B2 | 8/2013 | Istoc et al. |
| 8,533,475 B2 | 9/2013 | Frikart et al. |
| 8,545,483 B2 | 10/2013 | Schwabe et al. |
| 8,562,590 B2 | 10/2013 | Yodfat et al. |
| 8,568,357 B2 | 10/2013 | Ortega et al. |
| 8,573,027 B2 | 11/2013 | Rosinko et al. |
| 8,601,465 B2 | 12/2013 | Bernstein et al. |
| 8,710,993 B2 | 4/2014 | Hayter et al. |
| 8,762,624 B2 | 6/2014 | Binz et al. |
| 8,768,717 B2 | 7/2014 | Blomquist |
| 8,801,655 B2 | 8/2014 | Mernoe et al. |
| 8,868,794 B2 | 10/2014 | Masoud et al. |
| 8,903,350 B2 | 12/2014 | Ebner et al. |
| 8,932,250 B2 | 1/2015 | Montgomery et al. |
| 8,936,565 B2 | 1/2015 | Chawla |
| 8,938,306 B2 | 1/2015 | Lebel |
| 8,977,883 B2 | 3/2015 | Imhof et al. |
| 8,986,253 B2 | 3/2015 | DiPerna |
| 8,992,475 B2 | 3/2015 | Mann et al. |
| 9,049,982 B2 | 6/2015 | Brukalo et al. |
| 9,065,720 B2 | 6/2015 | Allen et al. |
| 9,101,714 B2 | 8/2015 | Miyazaki et al. |
| 9,114,210 B2 | 8/2015 | Estes |
| 9,132,227 B2 | 9/2015 | Bryant, Jr. et al. |
| 9,143,941 B2 | 9/2015 | Wang et al. |
| 9,173,992 B2 | 11/2015 | Bengtsson et al. |
| 9,259,531 B2 | 2/2016 | Kamen et al. |
| 9,308,319 B2 | 4/2016 | Mernoe et al. |
| 9,381,297 B2 | 7/2016 | Brown et al. |
| 9,474,856 B2 | 10/2016 | Blomquist |
| 9,486,571 B2 | 11/2016 | Rosinko |
| 9,555,186 B2 | 1/2017 | Kruse |
| 9,565,718 B2 | 2/2017 | Swanson |
| 2001/0041869 A1 | 11/2001 | Causey et al. |
| 2002/0029776 A1 | 3/2002 | Blomquist |
| 2002/0040208 A1 | 4/2002 | Flaherty et al. |
| 2002/0128594 A1 | 9/2002 | Das et al. |
| 2003/0060765 A1 | 3/2003 | Campbell et al. |
| 2003/0065308 A1 | 4/2003 | Lebel et al. |
| 2003/0208113 A1 | 11/2003 | Mault et al. |
| 2003/0212364 A1 | 11/2003 | Mann et al. |
| 2004/0068230 A1 | 4/2004 | Estes et al. |
| 2004/0073095 A1 | 4/2004 | Causey et al. |
| 2004/0122353 A1 | 6/2004 | Shahmirian et al. |
| 2004/0193090 A1 | 9/2004 | Lebel et al. |
| 2004/0204673 A1 | 10/2004 | Flaherty |
| 2004/0235446 A1 | 11/2004 | Flaherty et al. |
| 2004/0260233 A1 | 12/2004 | Garibotto et al. |
| 2005/0060030 A1 | 3/2005 | Lashinski et al. |
| 2005/0065464 A1 | 3/2005 | Talbot et al. |
| 2005/0137530 A1 | 6/2005 | Campbell et al. |
| 2005/0171513 A1 | 8/2005 | Mann et al. |
| 2005/0177395 A1 | 8/2005 | Blomquist |
| 2005/0246416 A1 | 11/2005 | Blomquist |
| 2005/0277911 A1 | 12/2005 | Stewart et al. |
| 2006/0031094 A1 | 2/2006 | Cohen et al. |
| 2006/0173444 A1 | 8/2006 | Choy et al. |
| 2006/0253296 A1 | 11/2006 | Liisberg et al. |
| 2006/0272652 A1 | 12/2006 | Stocker et al. |
| 2007/0016170 A1 | 1/2007 | Kovelman |
| 2007/0016449 A1 | 1/2007 | Cohen et al. |
| 2007/0033074 A1 | 2/2007 | Nitzan et al. |
| 2007/0060869 A1 | 3/2007 | Tolle et al. |
| 2007/0060870 A1 | 3/2007 | Tolle et al. |
| 2007/0093786 A1 | 4/2007 | Goldsmith et al. |
| 2007/0156033 A1 | 7/2007 | Causey, III et al. |
| 2007/0185547 A1 | 8/2007 | Hoyme et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255348 A1 | 11/2007 | Holtzclaw |
| 2007/0258395 A1 | 11/2007 | Jollota et al. |
| 2008/0033357 A1 | 2/2008 | Mann et al. |
| 2008/0065007 A1 | 3/2008 | Peterson et al. |
| 2008/0065016 A1 | 3/2008 | Peterson et al. |
| 2008/0071580 A1 | 3/2008 | Marcus et al. |
| 2008/0076969 A1 | 3/2008 | Kraft et al. |
| 2008/0139910 A1 | 6/2008 | Mastrototaro et al. |
| 2008/0147004 A1 | 6/2008 | Mann et al. |
| 2008/0147050 A1 | 6/2008 | Mann et al. |
| 2008/0183060 A1 | 7/2008 | Steil et al. |
| 2008/0228056 A1 | 9/2008 | Blomquist et al. |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0300651 A1 | 12/2008 | Gerber et al. |
| 2008/0312584 A1 | 12/2008 | Montgomery et al. |
| 2009/0018495 A1 | 1/2009 | Panduro |
| 2009/0018779 A1 | 1/2009 | Cohen et al. |
| 2009/0024178 A1 | 1/2009 | Hennig |
| 2009/0030382 A1 | 1/2009 | Brandt et al. |
| 2009/0030733 A1 | 1/2009 | Cohen et al. |
| 2009/0043290 A1 | 2/2009 | Villegas et al. |
| 2009/0085768 A1 | 4/2009 | Patel et al. |
| 2009/0088731 A1 | 4/2009 | Campbell et al. |
| 2009/0150186 A1 | 6/2009 | Cohen et al. |
| 2009/0157202 A1 | 6/2009 | Roberts et al. |
| 2009/0163855 A1 | 6/2009 | Shin et al. |
| 2009/0177142 A1 | 7/2009 | Blomquist et al. |
| 2009/0177147 A1 | 7/2009 | Blomquist et al. |
| 2009/0212966 A1 | 8/2009 | Panduro |
| 2009/0227855 A1 | 9/2009 | Hill et al. |
| 2009/0240193 A1 | 9/2009 | Mensinger et al. |
| 2009/0270833 A1 | 10/2009 | DeBelser et al. |
| 2009/0275886 A1 | 11/2009 | Blomquist et al. |
| 2010/0030045 A1 | 2/2010 | Gottlieb et al. |
| 2010/0069890 A1 | 3/2010 | Gräskov et al. |
| 2010/0094251 A1 | 4/2010 | Estes |
| 2010/0121415 A1 | 5/2010 | Skelton et al. |
| 2010/0130933 A1 | 5/2010 | Holland et al. |
| 2010/0145262 A1 | 6/2010 | Bengtsson et al. |
| 2010/0152658 A1 | 6/2010 | Hanson et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0174230 A1 | 7/2010 | Istoc et al. |
| 2010/0174553 A1 | 7/2010 | Kaufman et al. |
| 2010/0198142 A1 | 8/2010 | Sloan et al. |
| 2010/0198143 A1 | 8/2010 | Estes et al. |
| 2010/0198520 A1 | 8/2010 | Breton et al. |
| 2010/0205001 A1 | 8/2010 | Knudsen et al. |
| 2010/0218132 A1 | 8/2010 | Soni et al. |
| 2010/0249530 A1 | 9/2010 | Rankers et al. |
| 2010/0262117 A1 | 10/2010 | Magni et al. |
| 2010/0274592 A1 | 10/2010 | Nitzan et al. |
| 2010/0280329 A1 | 11/2010 | Randløv et al. |
| 2010/0280442 A1 | 11/2010 | Shahmirian et al. |
| 2010/0298662 A1 | 11/2010 | Yu et al. |
| 2010/0298685 A1 | 11/2010 | Hayter et al. |
| 2010/0331651 A1 | 12/2010 | Groll |
| 2011/0004275 A1 | 1/2011 | Carbunaru et al. |
| 2011/0009846 A1 | 1/2011 | Istoc et al. |
| 2011/0033833 A1 | 2/2011 | Blomquist et al. |
| 2011/0040247 A1 | 2/2011 | Mandro et al. |
| 2011/0040251 A1 | 2/2011 | Blomquist et al. |
| 2011/0046697 A1 | 2/2011 | Gerber et al. |
| 2011/0050428 A1 | 3/2011 | Istoc |
| 2011/0071372 A1 | 3/2011 | Sloan et al. |
| 2011/0077493 A1 | 3/2011 | Shadforth et al. |
| 2011/0077963 A1 | 3/2011 | Knudsen et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |

(56) References Cited

U.S. PATENT DOCUMENTS

| | | |
|---|---|---|
| 2011/0105955 A1 | 5/2011 | Yudovsky et al. |
| 2011/0106050 A1 | 5/2011 | Yodfat et al. |
| 2011/0112505 A1 | 5/2011 | Starkweather et al. |
| 2011/0112506 A1 | 5/2011 | Starkweather et al. |
| 2011/0118699 A1 | 5/2011 | Yodfat et al. |
| 2011/0124996 A1 | 5/2011 | Reinke et al. |
| 2011/0125095 A1 | 5/2011 | Lebel et al. |
| 2011/0126188 A1 | 5/2011 | Bernstein et al. |
| 2011/0130746 A1 | 6/2011 | Budiman |
| 2011/0144586 A1 | 6/2011 | Michaud et al. |
| 2011/0144616 A1 | 6/2011 | Michaud et al. |
| 2011/0152770 A1 | 6/2011 | DiPerna et al. |
| 2011/0152824 A1 | 6/2011 | DiPerna et al. |
| 2011/0160654 A1 | 6/2011 | Hanson et al. |
| 2011/0160666 A1 | 6/2011 | Hanson et al. |
| 2011/0166544 A1 | 7/2011 | Verhoef et al. |
| 2011/0178461 A1 | 7/2011 | Chong et al. |
| 2011/0178462 A1 | 7/2011 | Moberg et al. |
| 2011/0184653 A1 | 7/2011 | Ray et al. |
| 2011/0190694 A1 | 8/2011 | Lanier, Jr. et al. |
| 2011/0205065 A1 | 8/2011 | Strachan et al. |
| 2011/0213225 A1 | 9/2011 | Bernstein et al. |
| 2011/0213306 A1 | 9/2011 | Hanson et al. |
| 2011/0230837 A1 | 9/2011 | Kamen et al. |
| 2011/0256024 A1 | 10/2011 | Cole et al. |
| 2011/0275410 A1 | 11/2011 | Caffey et al. |
| 2012/0013625 A1 | 1/2012 | Blomquist et al. |
| 2012/0013802 A1 | 1/2012 | Blomquist et al. |
| 2012/0016295 A1 | 1/2012 | Tsoukalis |
| 2012/0029433 A1 | 2/2012 | Michaud et al. |
| 2012/0030610 A1 | 2/2012 | Di Perna et al. |
| 2012/0059673 A1 | 3/2012 | Cohen et al. |
| 2012/0091813 A1 | 4/2012 | Spurlin et al. |
| 2012/0232520 A1 | 9/2012 | Sloan et al. |
| 2012/0330227 A1 | 12/2012 | Budiman et al. |
| 2013/0012878 A1 | 1/2013 | Blomquist |
| 2013/0018315 A1 | 1/2013 | Blomquist |
| 2013/0046281 A1 | 2/2013 | Javitt |
| 2013/0053816 A1 | 2/2013 | DiPerna et al. |
| 2013/0123745 A1 | 5/2013 | Simmons |
| 2013/0159456 A1 | 6/2013 | Daoud et al. |
| 2013/0204433 A1 | 8/2013 | Gupta et al. |
| 2013/0324928 A1 | 12/2013 | Kruse |
| 2013/0331790 A1 | 12/2013 | Brown et al. |
| 2013/0345625 A1 | 12/2013 | Causey, III |
| 2014/0054883 A1 | 2/2014 | Lanigan et al. |
| 2014/0094744 A1 | 4/2014 | Blomquist |
| 2014/0094764 A1 | 4/2014 | Blomquist |
| 2014/0095485 A1 | 4/2014 | Blomquist |
| 2014/0095499 A1 | 4/2014 | Blomquist |
| 2014/0171772 A1 | 6/2014 | Blomquist |
| 2014/0272042 A1 | 9/2014 | Gillette |
| 2014/0276419 A1 | 9/2014 | Rosinko et al. |
| 2014/0276556 A1 | 9/2014 | Saint et al. |
| 2014/0323961 A1 | 10/2014 | Blomquist et al. |
| 2014/0350371 A1 | 11/2014 | Blomquist et al. |
| 2014/0378898 A1 | 12/2014 | Rosinko |
| 2015/0073337 A1 | 3/2015 | Saint et al. |
| 2015/0182695 A1 | 7/2015 | Rosinko |
| 2015/0320933 A1 | 11/2015 | Estes |
| 2015/0352282 A1 | 12/2015 | Mazlish |
| 2016/0030669 A1 | 2/2016 | Harris et al. |
| 2016/0082188 A1 | 3/2016 | Blomquist |
| 2016/0199571 A1 | 7/2016 | Rosinko et al. |
| 2016/0271325 A1 | 9/2016 | Farnan et al. |

OTHER PUBLICATIONS

Gollakota et al., "They Can Hear Your Heartbeats: Non-Invasive Security for Implantable Medical Devices", Aug. 2011, SIGCOMM '11, 12 pages.

Application and File history for U.S. Appl. No. 14/583,274, filed Dec. 26, 2014. Inventor: Rosinko.

Search Report and Written Opinion dated Apr. 24, 2015 for PCT Application No. PCT/US2014/072429 filed Dec. 26, 2014, 13 pages.

Search Report and Written Opinion dated Apr. 14, 2015 for PCT Application No. PCT/US2014/072181 filed Dec. 23, 2014, 11 pages.

Application and File history for U.S. Appl. No. 14/581,461, filed Dec. 23, 2014. Inventor: Rosinko.

SAFETY PROCESSOR FOR A DRUG DELIVERY DEVICE

RELATED APPLICATIONS

This application is a continuation of application Ser. No. 14/581,461 filed Dec. 23, 2014, which claims the benefit of U.S. Provisional Application No. 61/920,940 filed Dec. 26, 2013, each of which is incorporated herein in its entirety by reference.

FIELD OF THE INVENTION

The present invention relates to wireless control of drug delivery devices and, more particularly, to a safety processor to increase the safety and reliability of wireless control of drug delivery devices with remote devices such as smartphones.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of infusion pumps that have been developed for the administration of insulin and/or other medicaments for those suffering from both type I and type II diabetes. Some pumps configured as portable infusion devices can provide continuous subcutaneous insulin injection and/or infusion therapy for the treatment of diabetes. Such therapy may include the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. patent application Ser. No. 13/838,617, U.S. patent application Ser. No. 13/827,707 and U.S. Pat. No. 8,287,495, each of which is incorporated herein by reference in its entirety. Such infusion pumps are often discretely located on or around a patient, such as beneath clothing or in a carrying pouch. Some infusion pumps are therefore adapted to be programmed with remote control devices that enable programming without directly interacting with a user interface of the pump. These remote controllers therefore enable a pump to be programmed more privately and comfortably. With the proliferation of handheld consumer electronic devices, such as smartphones, there is a desire to be able to utilize such devices as the remote controller for remotely programming an infusion pump device. However, medical devices and consumer electronics have vastly different safety and reliability profiles, such that use of such consumer electronic devices to program medical devices such as infusion pumps could present safety issues for the patient.

SUMMARY OF THE INVENTION

A system and method provide for enhanced reliability and safety of programming and/or operating a medical device, such as an infusion pump, with a remote control device, such as a mobile phone (e.g., a smartphone). A safety processor acts as an intermediary device between the smartphone and the medical device to review transmissions from the smartphone prior to the transmissions being delivered to the medical device. The safety processor can determine whether the smartphone is compatible with the medical device by checking the type and version of the smartphone as well as the versions of the operating software and/or firmware resident on the phone. The safety processor can also check whether the operating command entered into the smartphone is within acceptable parameters, such as whether a bolus request for an infusion pump is within an acceptable range. If the safety processor determines, for instance, that the smartphone is approved for use with the medical device and the operating command is acceptable, the command is delivered from the smartphone to the medical device.

In one embodiment, a safety processor facilitates safe and reliable communications between a remote control device such as a smartphone and a medical device such as an infusion pump. The safety processor can include a transmitter/receiver that facilitates communications with each device and a memory that stores information regarding approved remote control devices for use with the medical device and information pertaining to acceptable parameters for use of the medical device on a patient. The safety processor receives communications from the smartphone intended as operating commands for the medical device. The safety processor utilizes the information stored in memory to determine if it is appropriate to transmit the communication on to the medical device. If the communication is acceptable, it is sent to the medical device for execution on the device. If the communication is not acceptable due to, for example, an incompatible device sending the communication or an operating command outside of acceptable parameters, an error message can be sent back to the smartphone.

In one embodiment, a programming operation for a medical device, such as an infusion pump, with a remote control device, such as a smartphone, utilizes a safety processor to ensure safe and reliable programming. A programming operation for the medical device can be performed on the smartphone and transmitted to the safety processor as a request for an operation on the medical device. The safety processor reviews the request and determines if it is acceptable by, for example, checking compatibility of phone hardware with the medical device, checking compatibility of phone software with the medical device and determining if the programmed operation is within a range of acceptable parameters for operations on the medical device. If the request is deemed acceptable, it is communicated to the medical device, executed on the medical device, and a status update can be sent to the smartphone. If the request is not acceptable, a communication indicating that the request was not executed can be sent to the smartphone.

Certain embodiments are described further in the following description, examples, claims, and drawings. These embodiments will become more apparent from the following detailed description when taken in conjunction with the accompanying exemplary drawings.

DETAILED DESCRIPTION

Figure 1:
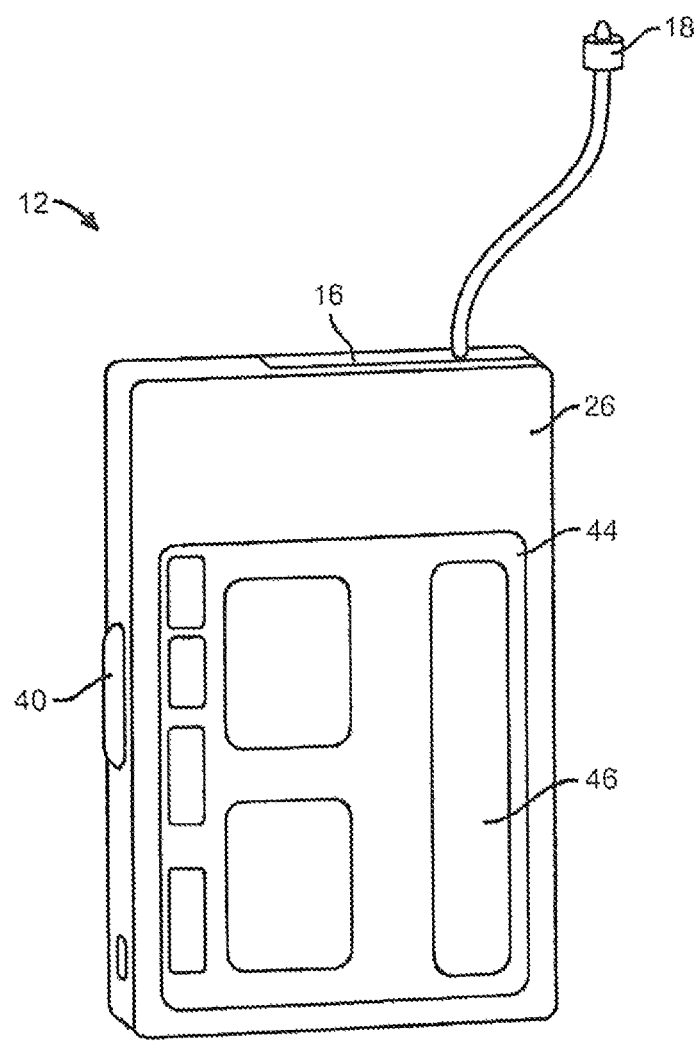
FIG. 1 is a medical device that can be utilized with embodiments of the present invention.

FIG. 1 depicts an embodiment of a medical device that can be used with embodiments of the present invention. In this embodiment, the medical device is configured as a pump 12 such as an infusion pump that can include a pumping or delivery mechanism and reservoir for delivering medicament to a patient and an output/display 44. The type of output/display 44 may vary as may be useful for a particular application. The type of visual output/display may include LCD displays, LED displays, plasma displays, graphene-based displays, OLED displays and the like. The output/display 44 may also be an interactive or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to a secondary display device such as a remote display, a remote control device, a laptop computer, personal computer, tablet computer, mobile communication device such as a smartphone or personal digital assistant (PDA) or the like.

Figure 2:
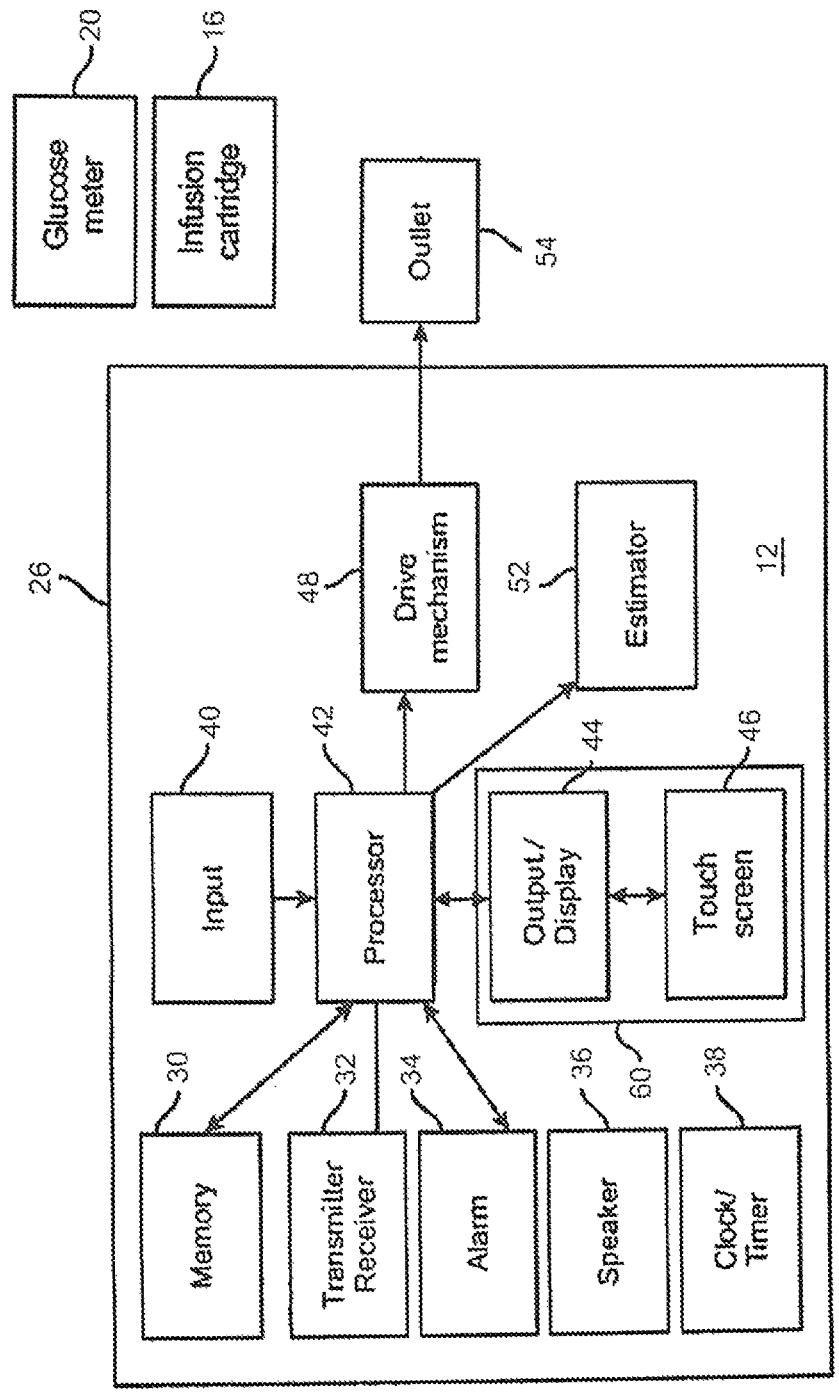
FIG. 2 is a block diagram representing a medical device that can be used with embodiments of the present invention.

In one embodiment, medical device can be a portable insulin pump configured to deliver insulin to a patient. Further details regarding such pump devices can be found in U.S. Patent Publication No. 2011/0144586, which is incorporated herein by reference in its entirety. In other embodiments, medical device can be an infusion pump configured to deliver one or more additional or other medicaments to a patient. In a further embodiment, the medical device can be a glucose meter such as a continuous glucose monitor. Further detail regarding such systems and definitions of related terms can be found in, e.g., U.S. Pat. Nos. 8,311,749, 7,711,402 and 7,497,827, each of which is hereby incorporated by reference herein in its entirety. In other embodiments, the medical device can monitor other physiological parameters of a patient. FIG. 2 illustrates a block diagram of some of the features that can be used with embodiments of the present invention, including features that may be incorporated within the housing 26 of a medical device such as a pump 12. The pump 12 can include a processor 42 that controls the overall functions of the device. The infusion pump 12 may also include a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters. In some embodiments, the processor 42 can communicate with a safety processor as disclosed herein.

Figure 3:
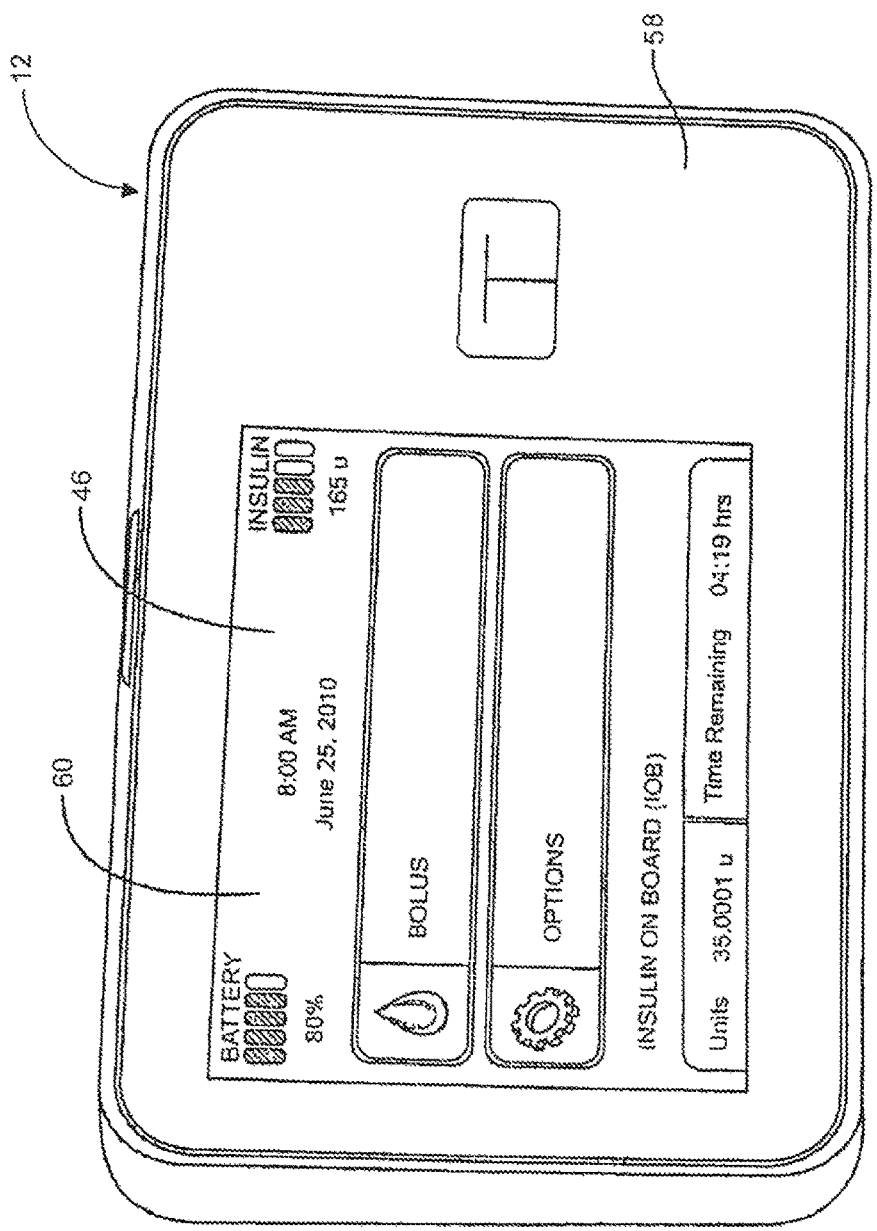
FIG. 3 depicts an exemplary screen shot of a home screen page of a user interface of a medical device such as an infusion pump that can be used with embodiments of the present invention.

Referring to FIG. 3, a front view of pump 12 is depicted. Pump 12 may include a user interface, such as, for example, a GUI 60 on a front surface 58 or other location of pump 12. GUI 60 may include a touch-sensitive screen 46 that may be configured for displaying data, facilitating data and/or command entry, providing visual tutorials, as well as other interface features that may be useful to a caregiver or to the patient operating pump 12. The GUI can also present alarms or alerts to the user.

Figure 7:
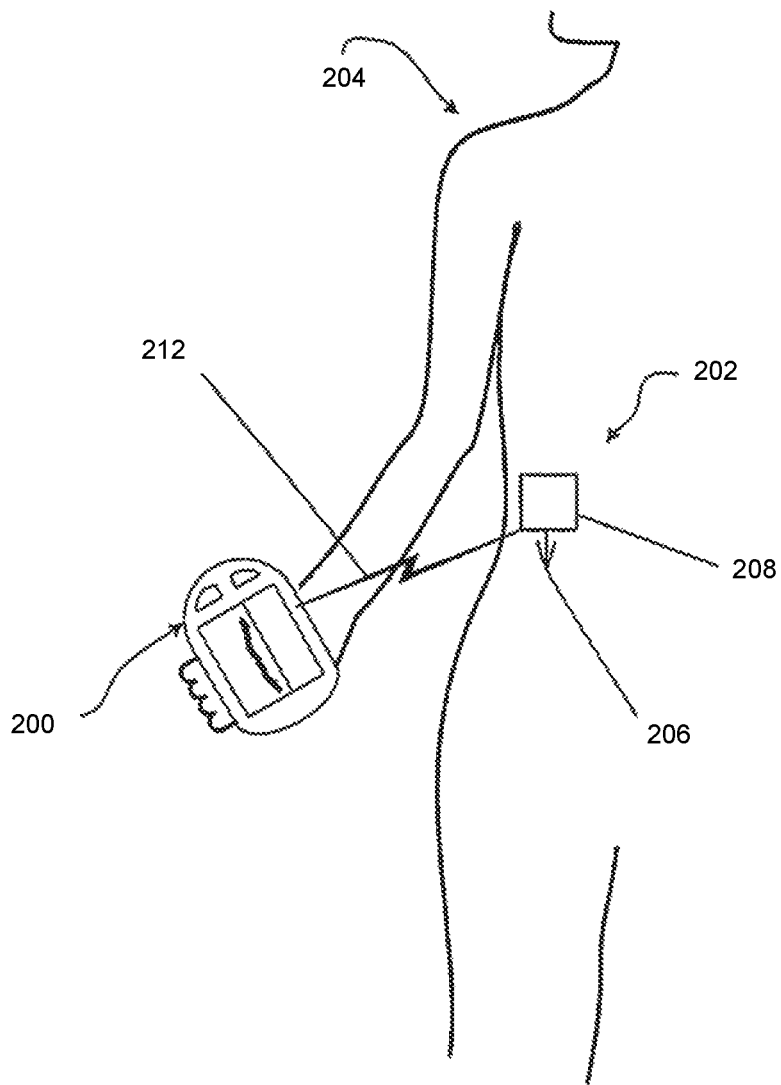
FIG. 7 is a partial schematic view depicting a continuous glucose monitor according to an embodiment of the present invention deployed on a patient.

Pump 12 can interface with a glucose meter, such as a continuous glucose monitor (CGM), that provides a substantially continuous estimated glucose level through a transcutaneous sensor that measures analytes, such as glucose, in the patient's interstitial fluid rather than the patient's blood. Referring to FIG. 7, an exemplary CGM system 200 according to an embodiment of the present invention is shown (other CGM systems can be used). The illustrated CGM system 200 includes a sensor 202 affixed to a patient 204 and is associated with the insulin infusion device 12. The sensor 202 includes a sensor probe 206 configured to be inserted to a point below the dermal layer (skin) of the patient 204. The sensor probe 206 is therefore exposed to the patient's interstitial fluid or plasma beneath the skin and reacts with that interstitial fluid to produce a signal that can be calibrated with the patient's blood glucose (BG) level. The sensor 202 includes a sensor body 208 that transmits data associated with the interstitial fluid to which the sensor probe is exposed. The data may be transmitted from the sensor 202 to the glucose monitoring system 200 via a wireless transmitter, such as a near field communication (NFC) radio frequency (RF) transmitter or a transmitter operating according to a "WiFi" or "Bluetooth" protocol or the like, or the data may be transmitted via a wire connector from the sensor 202 to the monitor system 200. Transmission of sensor data to the glucose monitor system 200 by wireless or wired connection is represented in FIG. 7 by the arrow line 212. Further detail regarding such systems and definitions of related terms can be found in, e.g., U.S. Pat. Nos. 8,311,749, 7,711,402 and 7,497,827, each of which is hereby incorporated by reference in its entirety.

In one embodiment, part of the CGM system 200 is incorporated into the pump 12 such that the processor 42 is adapted to receive the data from the sensor 202 and process and display the data on the display. In another embodiment, the CGM 200 is a separate device that communicates with the pump 12 through a wired or wireless link to transmit the CGM data to the pump 12.

In an embodiment of a pump 12 that communicates with a CGM and that integrates CGM data and pump data as described herein, the CGM can automatically transmit the glucose data to the pump. The pump can then automatically determine therapy parameters based on the data. For example, if the CGM data indicates that the user's blood glucose level is over a high blood glucose threshold level stored in memory, the pump can automatically calculate an insulin or other medicament bolus amount or an increase to a basal rate to bring the user's blood glucose level below the threshold or to a target value. As with other parameters related to therapy, such thresholds and target values can be stored in memory located in the pump or, if not located in the pump, stored in a separate location and accessible by the pump processor (e.g., "cloud" stored values accessible via a network connection). The pump processor can periodically and/or continually execute instructions for a checking function that accesses this data in memory, compares it with data received from the CGM and acts accordingly.

In one embodiment, such an automatic system for insulin delivery is referred to as an artificial pancreas system that provides closed loop or semi-closed loop therapy to the patient to approach or mimic the natural functions of a healthy pancreas. In such a system, insulin doses are calculated based on the CGM readings and are automatically delivered to the patient based on the CGM reading(s). For example, if the CGM indicates that the user has a high blood glucose level or hyperglycemia, the system can calculate an insulin dose necessary to reduce the user's blood glucose level below a threshold level or to a target level and automatically deliver the dose. Alternatively, the system can automatically suggest a change in therapy such as an increased insulin basal rate or delivery of a bolus, but can require the user to accept the suggested change prior to delivery. If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, suggest that the user, e.g., ingest carbohydrates and/or automatically take other actions and/or make other suggestions as may be appropriate to address the hypoglycemic condition, singly or in any desired combination or sequence. In some embodiments, multiple medicaments can be employed in such a system such as a first medicament, e.g., insulin, that lowers blood glucose levels and a second medicament, e.g., glucagon, that raises blood glucose levels.

Figure 4:
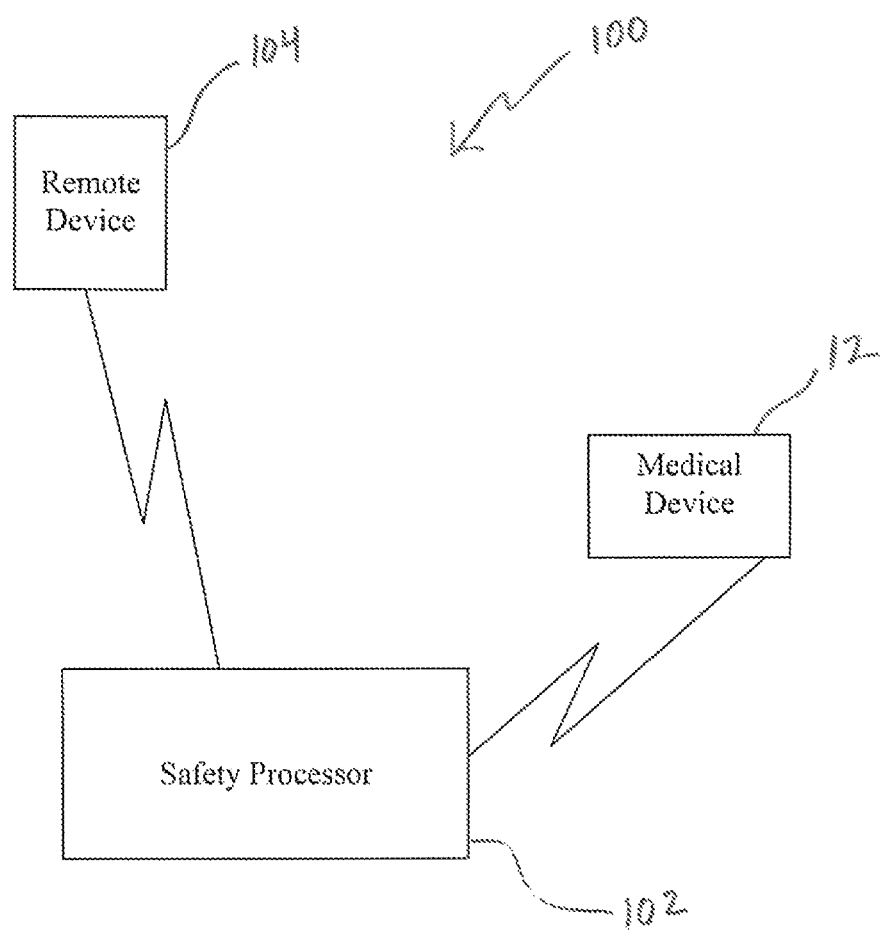
FIG. 4 is schematic representation of a system for remotely controlling a medical device according to an embodiment of the present invention.

Referring now to FIG. 4, a schematic representation of a system for facilitating safe and reliable communications between a medical device and an electronic device, such as a consumer electronic device, is depicted. System 100 includes a safety processor 102 that acts as an intermediary device between the medical device 12 and a consumer electronic device functioning as a remote control device 104 for the medical device 12. Operating and/or programming commands sent from the remote control device 104 and intended for execution by the medical device are first received by the safety processor 102 where they are reviewed before potentially being sent on to the medical device 12. In one embodiment, communications between the remote device 104 and the safety processor 102 and between the medical device 12 and the safety processor 102 are done wirelessly via, for example, Bluetooth®, Bluetooth® low energy, mobile or Wi-Fi communications. Alternatively or additionally, one or both of the medical device 12 and remote device 104 can communicate with the safety processor 102 over a wired connection. In certain embodiments, the remote device 104 and medical device 12 are precluded from communicating directly with each other such that all or selected communications must first go through the safety processor 102 before being relayed to the other device. In one embodiment, remote device 104 is a mobile phone such as a smartphone. In other embodiments, remote device 104 can be any device capable of running an application or other software adapted to enable programming of operating parameters for medical device 12 and communications with safety processor 102, such as, for example, an electronic tablet or a laptop or desktop computer.

Figure 5:
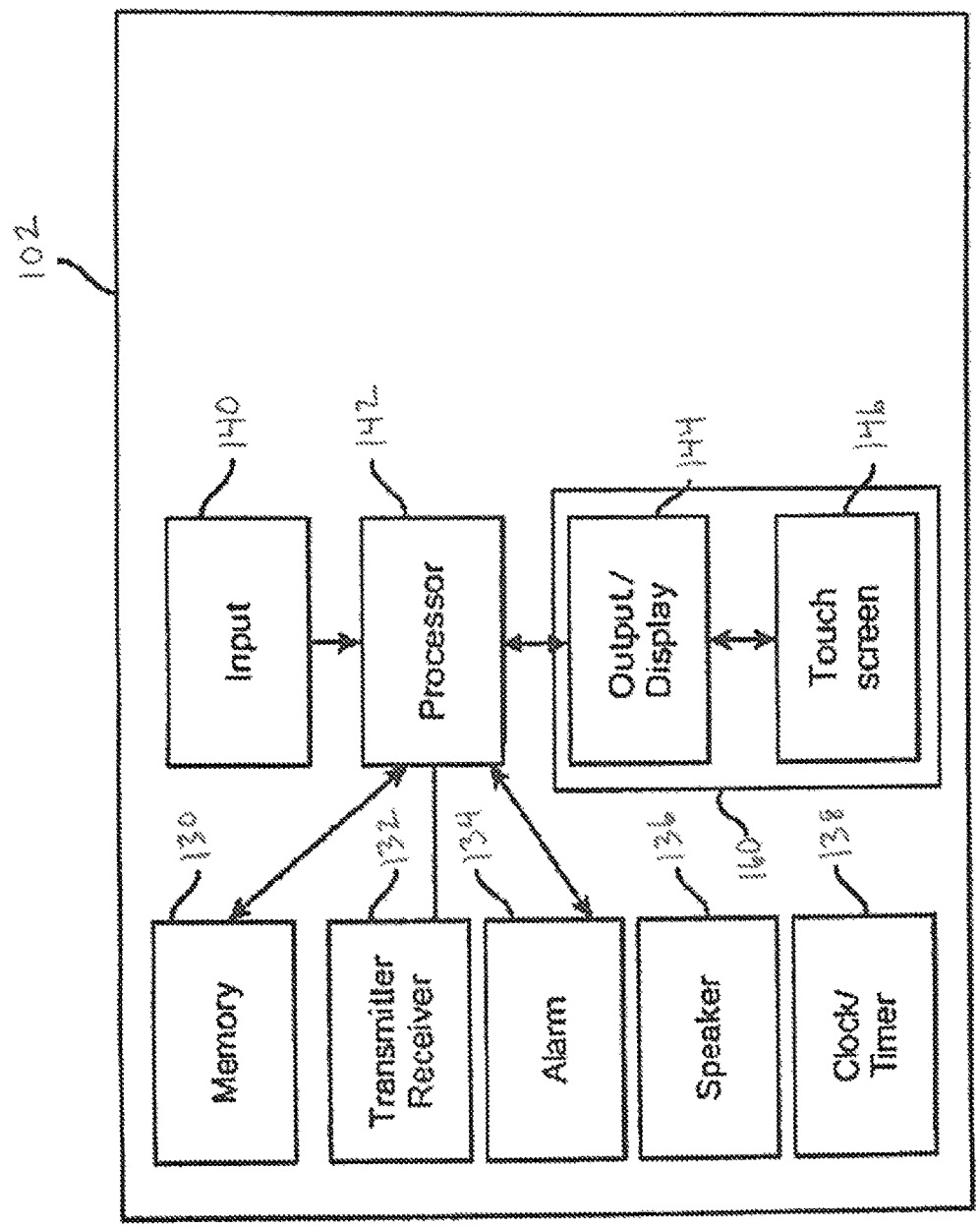
FIG. 5 is a block diagram representing a safety processor according to an embodiment of the present invention.

FIG. 5 depicts a block diagram of some features and components that can be associated with the safety processor 102. Safety processor 102 can include a processor 142 that controls the overall functions of the safety processor 102. The safety processor 102 can also include a memory device 130, a transmitter/receiver 132, an alarm system 134, a speaker 136, a clock/timer 138 an input device 140, and a user interface 160 having a display 144 and that, in some embodiments, can include a touch sensitive screen 146 with input capability. The processor 142 can communicate with the processor 42 of the pump 12 and a processor of the remote device 104 In some embodiments, the processor 142 may communicate with one or more processors of additional devices, for example, a continuous glucose monitor (CGM), display device, etc. through the transmitter/receiver. The processor 142 may also include programming that may allow the processor to receive signals and/or other data from an input device, such as a sensor that may sense pressure, temperature or other parameters.

Figure 6:
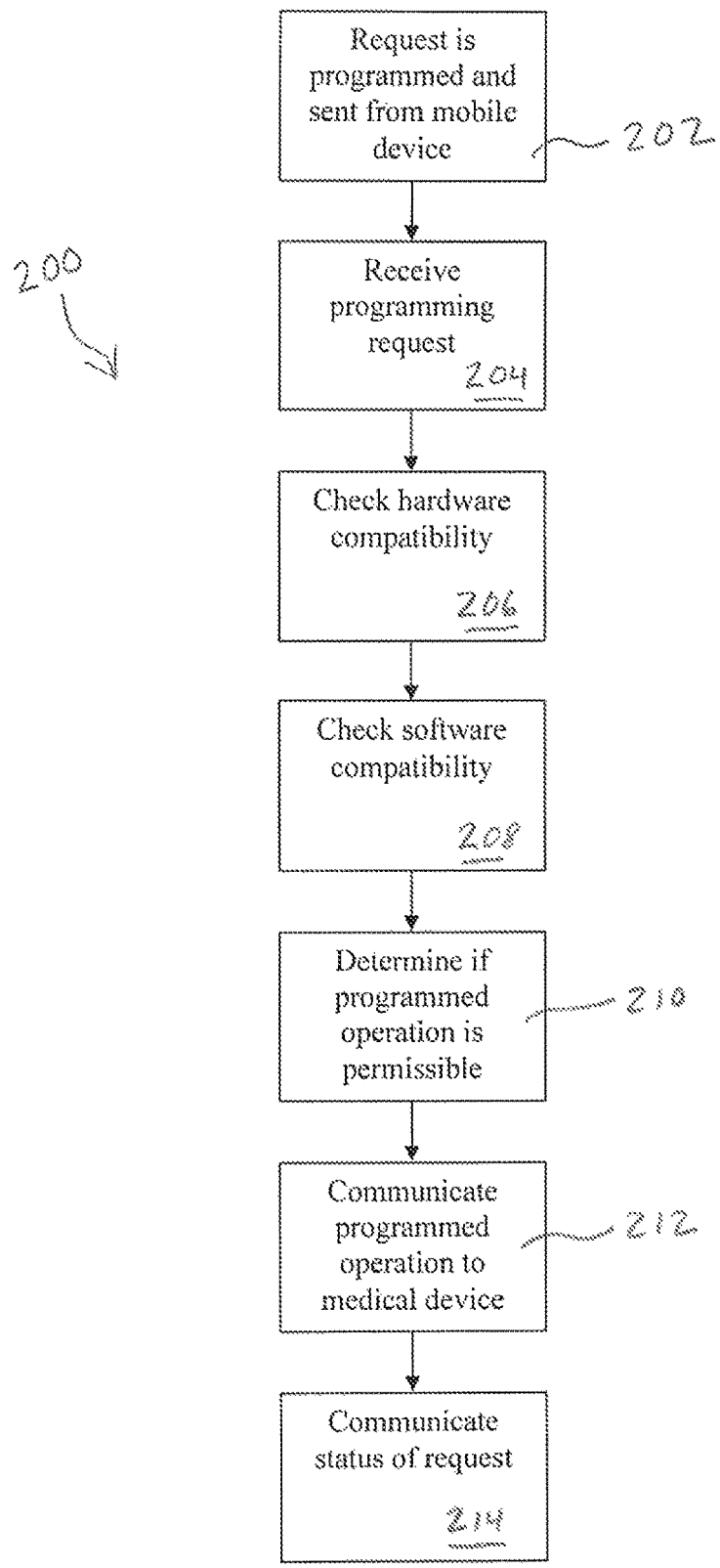
FIG. 6 is a flowchart of a method of facilitating safe and reliable communications between a medical device and a remote control device.

Referring now to FIG. 6, a flowchart is depicted of one example of a communications sequence 200 for operating medical device 12, such as an insulin pump, with a remote control device 104 through safety processor 102. At step 202, an operation request is entered into the remote control device 104 and transmitted to the safety processor 102. The operation request can relate to any type of operation that could otherwise be entered using the pump user interface or a dedicated remote controller such as, for example, delivery of a bolus, delivery or modification of a basal rate, review of pump history, programming of alarms, etc. The safety processor 102 receives the operation request at step 204. At steps 206 and 208, the safety processor 102 reviews the compatibility of the remote device 104 requesting the operation based on parameters stored in the safety processor memory 130. This can include hardware, software and/or firmware compatibility, such as whether the type of device is a device approved for use for controlling the medical device 12 and whether the type and/or version of the software being operated on the device for making the requests is approved.

Upon confirming compatibility of the remote device hardware, software and/or firmware, at step 210 the safety processor 102 can review the specific operation request in view of acceptable operation parameters or guidelines stored in memory to determine if the operation is permissible. For example, if the operation request is for delivery of a bolus of insulin or other medicament, the safety processor 102 can determine, for example, whether the size of the bolus is permissible, e.g., is below a maximum bolus value, and is being requested at an acceptable time after a previous bolus request. Similarly, a request to begin or modify basal insulin or other medicament delivery can be reviewed to determine if it is within an acceptable range. In certain embodiments, the acceptable parameters stored in the safety processor memory can be patient specific parameters. If the operation is permissible, safety processor 102 then communicates the programmed operation to the medical device 12 at step 212 and the medical device initiates the operation. The safety processor 102 can also monitor the operation to confirm its progress and determine when it is completed. In some embodiments, the safety processor 102 can require a confirmation from the remote device 104 prior to communicating the operation to the medical device 12. Finally, at step

214 the safety processor 102 can communicate with the remote device 104 to confirm the status of the request, including that the operation is in progress and/or completed, or that the request failed. In some embodiments, if a request has failed the safety processor 102 can provide a reason for the failure to the remote device 104, such as, for example, the bolus requested was larger than a maximum permissible bolus or the remote device 104 is not approved due to hardware, software and/or firmware incompatibility, etc.

In certain embodiments, safety processor 102 can also provide a number of other functions in addition to reviewing and transmitting communications between mobile device 104 and medical device 12. For example, as noted previously safety processor 102 can include an alarm system 134, speakers 136 and user interface 160. These features can be employed as part of a patient notification system. Such a system can include one or more of vibratory, audio (including natural language) and visual indicators to the patient of the progress of requests and/or errors, providing redundant and/or alternative notifications to those that may appear on the mobile device 104.

Safety processor 102 may be able to update its own software to, for example, provide an updated database of acceptable mobile device hardware and software/firmware versions with which the medical device is compatible and/or update the permissible operating parameters for the medical device. Such an update could be accomplished remotely through a wireless connection or through a wired connection. In some embodiments, software/firmware updates can occur automatically. In other embodiments, the safety processor 102 may notify the user through, for example, the user interface 160 of the safety processor 102 and/or the mobile device 104, that a software and/or firmware update is available and request that the user initiate the update at the safety processor 102 or the mobile device 104. In addition, in some embodiments the mobile device 104, prior to a software and/or firmware upgrade, may be able to communicate with the safety processor 102 to have the safety processor 102 confirm that the upgrade will be compatible with the system to allow programming of the medical device 12.

In some embodiments, the safety processor 102 can include features enabling programming of the medical device 12 directly from the safety processor 102. This can provide an additional means for operation of the medical device 12 if the remote device 104 is unavailable or has been deemed or determined to be incompatible with the medical device 12. The safety processor 102 can be provided with functionality to control all aspects of the medical device 12, or with a more limited set of features. For example, in one embodiment, the safety processor is only capable of programming a bolus of medicament such as insulin for delivery to the patient.

Safety processor 12 can also communicate with alternative or additional devices and, in some embodiments, act as an intermediary between the remote device 104 and those other devices and/or the medical device 12 and those other devices. Such devices include, for example, glucose meters, continuous glucose monitors and monitors for other physiological parameters.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 and 8,448,824; commonly owned U.S. Patent Publication Nos. 2009/0287180; 2010/0008795; 2010/0071446; 2010/0218586; 2012/0123230; 2013/0053816; 2013/0159456; 2013/0306191; 2013/0324928; 2013/0332874; 2013/0283196; 2013/0331790; 2013/0331778; 2014/0276531; 2014/0276419; 2014/0276420; 2014/0276423; 2014/0276409; 2014/0276537; 2014/0276553; 2014/0276569; 2014/0276570; 2014/0276571; 2014/0276574; 2014/0276556; 2014/0276538; and commonly owned U.S. Patent Application Publication Nos. 2014/0378898; 2015/0073337; and 2015/0072613 and commonly owned U.S. Provisional Application Ser. Nos. 61/911,576, 61/920,902, 61/920,914, 61/920,932; 61/920,940; 61/990,501; and 62/030,933.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An apparatus for reviewing medicament delivery commands for a system providing closed loop therapy to a patient with an ambulatory infusion pump, comprising:
a memory adapted to store at least one acceptable operation parameter for closed loop delivery of medicament with an ambulatory infusion pump;
a processor communicatively coupled with the memory, the processor configured to:
communicate with a device that calculates at least one medicament delivery parameter for delivery of medicament to a patient in a closed loop system based at least in part on data relating to glucose levels of the patient;

review one or more medicament delivery parameters calculated for delivery of medicament in the closed loop system;

determine whether it is permissible for the ambulatory infusion pump to deliver the medicament according to the one or more medicament delivery parameters based on the at least one acceptable operation parameter for closed loop delivery of medicament with the ambulatory infusion pump stored in the memory; and enable the ambulatory infusion pump to deliver the medicament according to the one or more medicament delivery parameters if it is determined that it is permissible for the ambulatory infusion pump to deliver the medicament according to the one or more medicament delivery parameters.

2. The device of claim 1, wherein the device that calculates the at least one medicament delivery parameter is a remote control device of the closed loop therapy system.

3. The device of claim 1, wherein the device that calculates the at least one medicament delivery parameter is the ambulatory infusion pump.

4. The device of claim 1, wherein the at least one medicament delivery parameter is a modification to an ongoing medicament delivery to the user.

5. The device of claim 4, wherein the ongoing medicament delivery is delivery of a basal rate.

6. The device of claim 1, wherein the processor is configured to prohibit the ambulatory infusion pump from delivering the medicament according to the one or more medicament delivery parameters if the processor determines that it is not permissible for the ambulatory infusion pump to deliver the medicament according to the one or more medicament delivery parameters.

7. The device of claim 6, wherein the processor is configured to determine that it is not permissible for the ambulatory infusion pump to deliver the medicament according to the one or more medicament delivery parameters if an amount of one or more of the medicament delivery parameters is not below a maximum permissible value.

8. The device of claim 6, wherein the processor is configured to determine that it is not permissible for the ambulatory infusion pump to deliver the medicament according to the one or more medicament delivery parameters if an amount of one or more of the medicament delivery parameters is not within an acceptable range.

9. The device of claim 6, wherein the processor is configured to determine that it is not permissible for the ambulatory infusion pump to deliver the medicament according to the one or more medicament delivery parameters if a timing of delivery of one or more medicament delivery parameters is not acceptable.

10. The device of claim 6, wherein the processor is further configured to provide a notification to the patient if the processor determines that it is not permissible for the ambulatory infusion pump to deliver the medicament according to the one or more medicament delivery parameters.

11. A system for providing closed loop therapy to a patient with an ambulatory infusion pump, comprising:

an ambulatory infusion pump;

a device configured to receive data relating to glucose levels of the patient and calculate at least one medicament delivery parameter for delivery of medicament to the patient based on the data relating to glucose levels; and a safety processor configured to communicate with the device to receive and review one or more medicament delivery parameters calculated by the device, determine whether it is permissible for the ambulatory infusion pump to deliver the medicament according to the one or more medicament delivery parameters based on at least one acceptable operation parameter for closed loop delivery of medicament with the ambulatory infusion pump, and enable the ambulatory infusion pump to deliver the medicament according to the one or more medicament delivery parameters if it is determined that it is permissible for the ambulatory infusion pump to deliver the medicament according to the one or more medicament delivery parameters.

12. The system of claim 11, wherein the device configured to receive data relating to glucose levels of the patient and calculate at least one medicament delivery parameter for delivery of medicament to the patient based on the data relating to glucose levels is incorporated into the ambulatory infusion pump.

13. The system of claim 11, wherein the device configured to receive data relating to glucose levels of the patient and calculate at least one medicament delivery parameter for delivery of medicament to the patient based on the data relating to glucose levels is a separate device from the ambulatory infusion pump.

14. The system of claim 13, wherein the device is a remote control device for the ambulatory infusion pump.

15. The system of claim 11, wherein the at least one medicament delivery parameters is a modification to an ongoing medicament delivery to the user.

16. The system of claim 15, wherein the ongoing medicament delivery is delivery of a basal rate.

17. The system of claim 11, wherein the safety processor is configured to prohibit the ambulatory infusion pump from delivering the medicament according to the one or more medicament delivery parameters if the safety processor determines that an amount of one or more of the medicament parameters is not permissible.

18. The system of claim 17, wherein the safety processor is configured to determine that the amount of one or more of the medicament parameters is not permissible if the amount is not below a maximum permissible value or is not within an acceptable range.

19. The system of claim 11, wherein the safety processor is configured to prohibit the ambulatory infusion pump from delivering the medicament according to the one or more medicament delivery parameters if the safety processor determines that a timing of delivery of one or more medicament parameters is not acceptable.

20. The system of claim 11, wherein the safety processor is further configured to provide a notification to the patient if it is determined that it is not permissible for the ambulatory infusion pump to deliver the medicament according to the one or more medicament delivery parameters.

* * * * *